United States Patent [19]

Cragg

[11] Patent Number: 5,370,653
[45] Date of Patent: Dec. 6, 1994

[54] THROMBECTOMY METHOD AND APPARATUS

[75] Inventor: Andrew H. Cragg, Bloomington, Minn.

[73] Assignee: Micro Therapeutics, Inc., Aliso Viejo, Calif.

[21] Appl. No.: 95,867

[22] Filed: Jul. 22, 1993

[51] Int. Cl.$^5$ ............................................. A61B 5/00
[52] U.S. Cl. .................................... 606/170; 128/756
[58] Field of Search .............. 128/756; 606/159, 167, 606/170, 171, 180; 604/22

[56] References Cited

U.S. PATENT DOCUMENTS

| | | | |
|---|---|---|---|
| 2,712,823 | 7/1955 | Kurtin | 606/180 X |
| 2,911,660 | 11/1959 | Klemas et al. | 606/180 X |
| 3,435,826 | 4/1969 | Fogarty | 128/348 |
| 3,525,339 | 8/1970 | Halligan | 606/159 |
| 4,227,537 | 10/1980 | Suciu et al. | 128/756 |
| 4,465,072 | 8/1984 | Taheri | 606/159 |
| 4,646,736 | 3/1987 | Auth | 128/363 R |
| 4,692,139 | 8/1987 | Stiles | 604/22 |
| 4,842,579 | 6/1989 | Shiber | 604/22 |
| 4,966,162 | 10/1990 | Wang | 128/750 |
| 5,009,659 | 4/1991 | Hamlin et al. | 606/159 |
| 5,011,488 | 4/1991 | Ginsberg | 606/180 X |
| 5,085,635 | 2/1992 | Cragg | 604/96 |
| 5,100,424 | 3/1992 | Jang et al. | 606/159 |
| 5,102,415 | 4/1992 | Guenther et al. | 606/159 |
| 5,135,484 | 8/1992 | Wright | 604/28 |
| 5,141,491 | 8/1992 | Bowald | 604/22 |
| 5,192,290 | 3/1993 | Hilal | 606/159 |

Primary Examiner—Max Hindenburg
Attorney, Agent, or Firm—Joseph F. Breimayer

[57] ABSTRACT

A thrombectomy method and apparatus for dissolving a soft fibrinous obstruction, such as a recently formed thrombus, within a patient's vascular system, either in a vessel or in a prosthetic implant, employing a rotating brush for separating and mixing the fibrin of the thrombus while a dissolving agent, e.g. streptokinase or urokinase, is introduced and mixed in and applied to the separated fibrin. The brush is formed of soft, flexible bristles that extend outward from the distal end of an elongated, flexible, rotatable drive shaft having a drive motor assembly attached at its proximal end. In use, an introducer catheter is introduced through a patient's blood vessels until the distal end opening is positioned adjacent the thrombus. The brush is passed through the introducer lumen and out the distal opening to place the brush bristles in contact with the thrombus. The dissolving agent is introduced into the region of rotation of the brush either through the introducer catheter lumen or a drive shaft lumen for dissolving the soft thrombus as it is mixed by the bristles. The bristles are sufficiently resilient and dimensioned for ease of introduction and mixing into the fibrin of the soft thrombus, while not damaging the vessel wall. Optionally, a balloon catheter or a mesh basket may be coaxially introduced through the drive shaft lumen and placed downstream to restrain fragments and to allow the dissolving agent to complete the dissolution thereof.

37 Claims, 3 Drawing Sheets

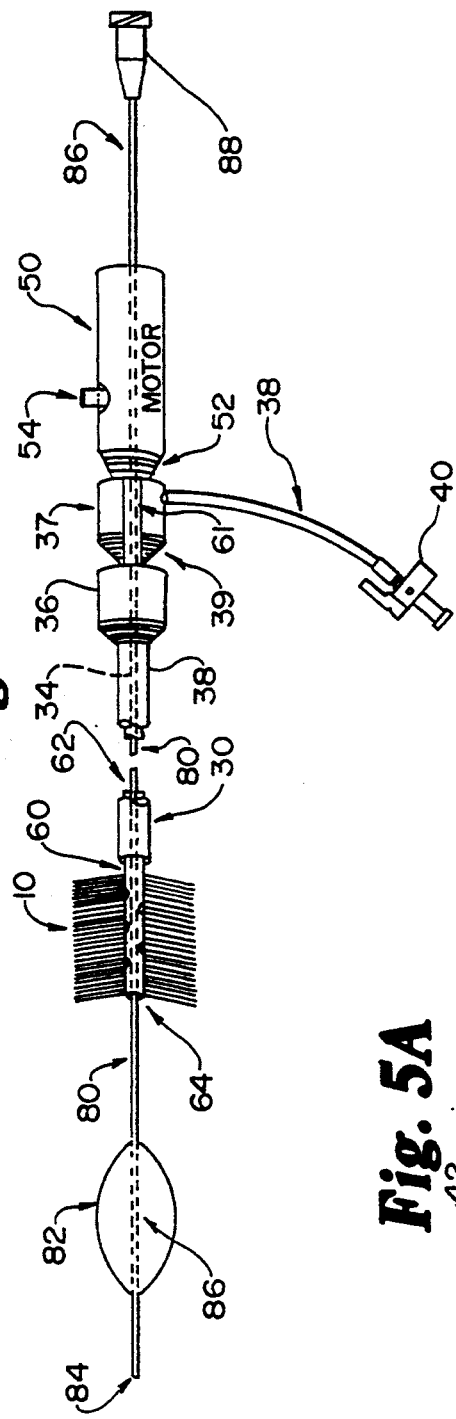
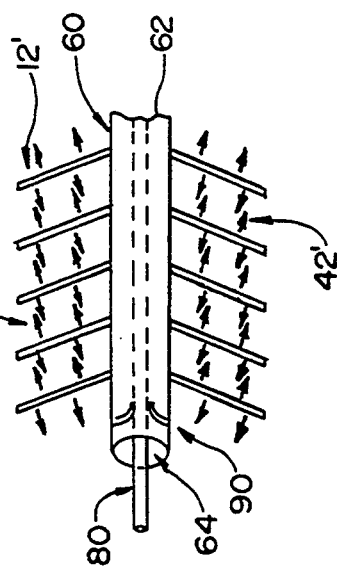
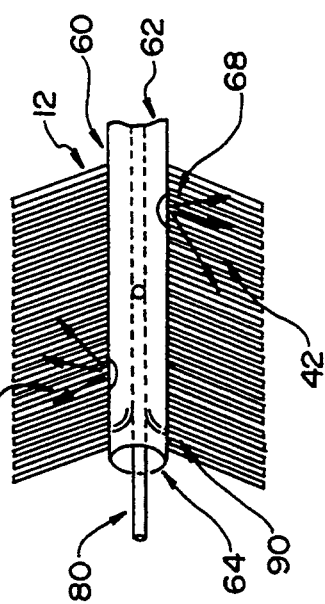

THROMBECTOMY METHOD AND APPARATUS

BACKGROUND OF THE INVENTION

1. Field of the Invention

The present invention relates to a thrombectomy method and apparatus for removing a soft, newly formed thrombus or blood clot from a blood vessel, and particularly to the application of an obstruction dissolving agent into the fibers of the obstruction as the fibers are mixed and exposed by a soft, flexible rotating brush for fragmenting and dissolving the fragments of the obstruction in situ.

2. Description of the Background Art

The acute symptoms of blockage of a vein at a venous valve or a partially sclerosed and narrowed artery may be instigated by the presence of a soft blood clot which may either form at the site or form elsewhere, as through trauma or injury to the vascular system, at a cardiac valve or at the site of an access fistula for enabling chronic hemodialysis and be carried to the site by the flow of blood. In the venous and arterial blood vessels, such clots are referred to as an embolus or emboli and a thrombus or thrombi, respectively. Emboli and thrombi are characterized by a soft consistency that maintains a form and is resistant to dissolution in the bloodstream or in water and entraps red blood cells. Under the microscope it can be seen that this clotting behavior is effected by strands of fibrin which are formed of normally soluble fibrinogen molecules which undergo a conversion to stranded fibrin in response to a chemical released at the site of an injury to a blood vessel wall in order to prevent the loss of blood through the injured wall. Recently formed blood clots stabilized in position as emboli and thrombi are soft and jelly-like in consistency and are readily penetrated but reform after the penetrating object is removed.

The invasive removal of both soft and hard obstructions from arteries and prostheses implanted to substitute for diseased arteries or to retain arteries open to blood flow has become commonplace. Over many years, a patient's arterial system may become narrowed and eventually occluded with relatively hard, calcified plaque resulting in reduced blood flow and consequent oxygen deprivation, to organs and muscles supplied by the arterial system. The progress of atherosclerosis in a given patient may not be diagnosed until the onset of an ischemic episode triggering the symptoms of chest pain or heart failure, with respect to cardiac arteries, or a stroke or eyesight failure, if the carotid artery or its tributaries are blocked. Usually, the cardiac arteries in patients that suffer ischemia and have become blocked slowly over the years develop collateral blood vessels that take over or share the burden of supplying oxygen to the myocardium. However, as the disease is progressive, the arterial system eventually becomes incapable of sustaining that burden resulting in myocardial infarction. In the peripheral arteries, a blockage of oxygen carrying blood may cause pain or the onset of gangrene resulting in amputation of the limb or eventual death.

When blockage takes place, the patient is at risk of death or serious myocardial infarction or paralysis unless the blockage is promptly eliminated. Once diagnosed, treatments are first undertaken to remove the soft obstruction and restore the blood flow. Once the soft obstruction is removed, drug therapy may be instituted and the patient may undergo coronary artery bypass graft surgery to replace the occluded cardiac arteries with vein sections sacrificed from the patient's peripheral venous system or with artificial grafts. Alternatively, the occlusions in the arteries may be expanded through balloon angioplasty, and artificial stents may be implanted to brace the expanded arterial wall. Other techniques for removing the obstruction occluding the vessel include invasively abrading or cutting away the built up placque and aspirating the fragments out of the bloodstream with mechanical atherectomy tools are described in U.S. Pat. No. 4,842,579 to Shiber. In addition catheter systems employing laser energy are also being clinically used. In the carotid artery, the occlusion may have to be excised by surgical endorevectomy.

With respect to the venous system, emboli may collect at constrictions or valves in the relatively slow moving bloodstream. Emboli obstructing major venous valves creates a back pressure in the circulatory system so as to reduce blood flow even in the arterial system. Trapped venous blood causes swelling of the limb and the combination of swelling and reduced arterial blood flow may itself threaten the viability of the limb. Treatment for this condition involves long term use of anticoagulation drugs to attempt to reduce the formation of new emboli.

The acute treatments that are undertaken to remove thrombi or emboli take many forms. At the onset of serious symptoms, the site of obstruction is identified with radiographic agents introduced into the bloodstream in a diagnostic radiographic procedure of the type described in my U.S. Pat. No. 5,085,635. Then dissolving agents, e.g. streptokinase or urokinase, may be infused through catheters which are introduced into the venous system and advanced until the infusion port at the distal end of the catheter is situated adjacent to the blockage. The dissolving agent is infused slowly over a matter of hours while the patient is monitored. At safe low dosages, this procedure is time consuming and requires careful monitoring of the risk of bleeding.

Other treatments have been proposed for mechanically entrapping and removing stabilized thrombi, including the use of the "Fogarty catheter" or inflatable balloon embolectomy catheter of the type disclosed in U.S. Pat. No. 3,435,826 to Fogarty. Typically, the balloon catheter is guided with the balloon collapsed through and into a location distal to the thrombus. The balloon is expanded and withdrawn in order to dislodge the thrombus and pull it along and out the incision in a blood vessel. In using this procedure, a risk exists that all or a portion of the thrombus will dislodge and travel to a further restriction in the arterial system.

Various other embolectomy/thrombectomy catheters and methods have been proposed, including the use of an elastomeric foam at the distal tip, rather than an expandable balloon, as disclosed in U.S. Pat. No. 5,192,290 to Hilal. In U.S. Pat. No. 4,646,736 to Auth, it is proposed that a coiled wire be passed through a blood clot and rotated to catch and wind the fibrin structure while withdrawing blood or introducing a dissolving agent, e.g. streptokinase. In U.S. Pat. No. 4,692,139 to Stiles, it is proposed to employ the combination of ultrasound and a dissolving agent infused into a blood clot to emulsify and fragment the fibrin structure of the clot and to aspirate the fragments.

In use of such equipment, it is not possible to determine if the entire thrombus has been trapped or all fragments have been aspirated. Employing various techniques, accelerated atherosclerosis or internal hyperplasia has been reported at the removal site.

Despite the advances and improvements in treatment that have been introduced in recent years, a need remains for an embolectomy/thrombectomy apparatus and method that is simple to practice, does not threaten the integrity of the vessel, and wherein the vessel patency is rapidly restored.

SUMMARY OF THE INVENTION

In view of the apparent interchangeable use in the background art, only the terms soft fibrinous obstruction or thrombus and thrombectomy will be employed in the remaining description of the invention and the claims, and it will be understood that these terms shall embrace and be the equivalent of blood clot or embolus and embolectomy, respectively, and are applicable to the removal of soft, recently formed thrombi or blood clots.

It is a principal object of the present invention to provide a thrombectomy apparatus and method which provides for the dissolution of a soft, recently formed thrombus in situ without the necessity of depending on aspirating or trapping and removing fragments.

It is a further object of the present invention to effect a thrombectomy in situ through mixing and presentation of the fibrin of the thrombus to an infused dissolving agent so that as the fibrin surface is exposed, it tends to dissolve.

In accordance with these and other objects, a thrombectomy system for dissolving a soft fibrinous blood clot obstructing a patient's vascular system, either in a patent vein or artery or in a prosthetic implant, employs a soft rotating brush for separating and mixing the fibrin of the obstruction while a dissolving agent, e.g. streptokinase or urokinase, is introduced and mixed in and applied to the separated fibrin.

In use, the thrombectomy system includes an introducer catheter introduced and advanced through a patient's blood vessels until the distal end is positioned adjacent a soft fibrinous obstruction, and an elongated, flexible, rotatable drive shaft having a drive motor attached at its proximal end, the drive shaft passed through the introducer lumen to place a brush attached to the drive shaft distal end in contact with the soft obstruction. The brush has soft, flexible bristles extending outward from the drive shaft distal end, the bristles being sufficiently resilient and dimensioned for enabling compression and passage of the brush out of and back into the distal end of the introducer lumen and effective to mix into the fibrin of the soft obstruction yet not damage the vessel wall. The dissolving agent is introduced during rotation of the brush, either through a lumen of the introducer or the drive shaft, and out exit ports at the distal ends thereof in the region of rotation of the brush for dissolving the soft obstruction as it is contacted by the bristles. Alternatively, the bristles are hollow and are coupled to the drive shaft lumen to emit the dissolving agent through the bristles as they pass through the soft fibrin of the obstruction.

In order to contain released fragments so that the dissolving agent may complete dissolution, the brush may be introduced through the soft obstruction downstream and rotated as the brush is slowly retracted through the obstruction. Optionally, a balloon catheter or a mesh basket may be coaxially introduced through the drive shaft lumen and placed downstream to temporarily obstruct the blood and dissolving agent flow away from the site and restrain fragments to allow the concentrated dissolving agent to complete the dissolution thereof.

Advantageously, blood clots and thrombi are more readily dissolved by the mixing action of the brush bristles as the dissolving agent is introduced. Intimal hyperplasia and the risk of vessel wall rupture or pseudoneurism is decreased by use of the soft brush bristles. The speed of dissolution may be reduced to minutes, in comparison with hours for introduction of the dissolving agent alone. The reduced amount of dissolving agent introduced decreases the risk of internal bleeding. Patient comfort is increased and cost of the intensive care treatment is reduced by the shortened time and reduction of exposure to the dissolving agent.

BRIEF DESCRIPTION OF THE DRAWINGS

These and other objects, advantages and features of the invention will become apparent from the following detailed description of the preferred embodiments of the invention, in which:

FIG. 5 is a view of the assembled components of a third embodiment of the invention;

FIG. 5A is a detailed, enlarged view of the distal brush and catheter of the embodiment of FIG. 5; and FIG. 6 is a view of a further embodiment of the brush and infusion components suitable for substitution in the embodiments of FIGS. 4 and 5 of the invention.

Figure 1A:
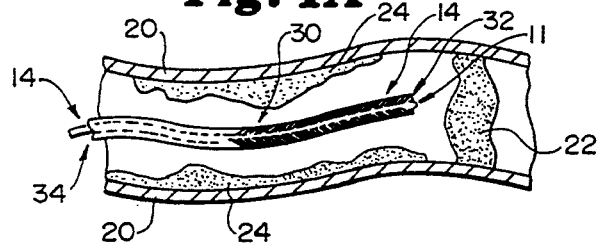
FIGS. 1A–1D are illustrations of the steps of introducing a brush proximally or distally through a soft, recently formed, thrombus, rotating the brush, infusing a dissolving agent and withdrawing the brush from the region of the dissolved thrombus in accordance with the invention.

The drawing figures are not necessarily to scale.

DETAILED DESCRIPTION OF THE PREFERRED EMBODIMENTS OF THE INVENTION

In the following description, the several alternative preferred embodiments share common features of the invention which are illustrated generally in FIGS. 1A–1D. These illustrations depict very generally the method and apparatus of the invention including the steps of introducing a brush 10 into a blood vessel 20 and into contact with a thrombus 22, rotating the brush 10 to expose the strands of fibrin forming the thrombus while infusing a dissolving agent into the thrombus 22, and withdrawing the brush 10 from the vessel 20.

FIGS. 1A–1D are intended to show the apparatus of and method of the invention in a general fashion encompassing the various embodiments described hereafter. The brush 10 and the manner of introducing the dissolving agent illustrated in FIGS. 1A–1D are thus not intended to be of any particular configuration or method, insofar as the various embodiments disclosed hereafter are substitutable for the particular configuration generally depicted. In these illustrations, the brush 10 attached at the distal end of a drive shaft 14 comprises bristles 12 which extend distally and radially around the drive shaft 14 near the distal shaft tip 11. The bristles 12 could extend perpendicularly and/or proximally to the drive shaft 14.

The introduction of the brush 10 is facilitated by an introducer catheter 30 which is inserted and advanced percutaneously through the vascular system in a manner well known in the catheterization art until the distal end opening 32 of the catheter lumen 34 is positioned adjacent to the thrombus 22 at the radiographically identified obstruction site in the vessel 20. The distal end 32 of the introducer catheter 30 may be positioned either proximally as shown in FIG. 1A or distally, by passing it through the soft thrombus 22, as shown in FIG. 1B.

Figure 1B:
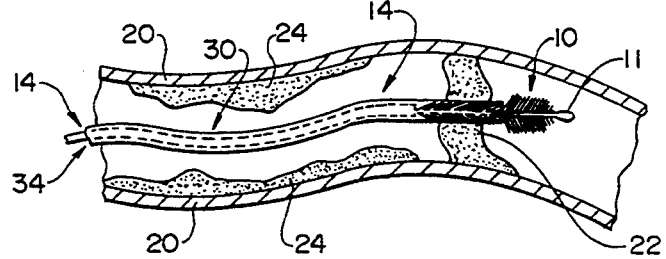
Figure 1C:
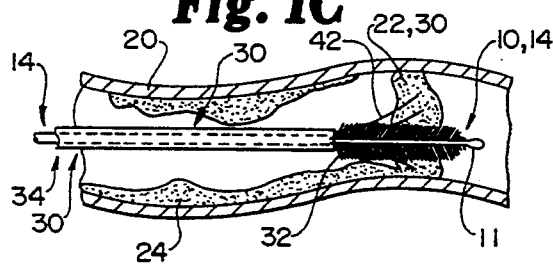

Following the positioning of the distal opening 32 at the position shown in FIG. 1A, the brush 10 and drive shaft 14 are advanced distally in the introducer catheter lumen 34 until the brush 10 is advanced out the distal opening 32 and extends into or through the thrombus 22 in the manner shown in FIG. 1C. Alternatively, in the position of FIG. 1B, the brush 10 is advanced distally out the distal opening 32, and the introducer is retracted to the position shown in FIG. 1C. The drive shaft 14 is positioned to be rotated and retracted back through the thrombus 22.

After the brush 10 is so positioned, the drive shaft 14 may be advanced or retracted, depending on the position of introduction, and is rotated by a drive motor coupled to its proximal end so that the bristles 12 sweep through the fibrin of the thrombus 22. At the same time, the dissolving agent is infused into the site by its passage through the introducer lumen 34 at a rate of about 2–250 ml/hour. As the bristles sweep over and through the thrombolytic mass, they separate strands or fibrin of the thrombus, so that they are progressively and repetitively mixed with and exposed to the infused dissolving agent. This mixing exposure speeds the operation of the dissolving agent and reduces the total amount introduced. After a period of such treatment, the thrombus becomes completely dissolved. The progress of the procedure is monitored radiographically by injecting small amounts of contrast material with the dissolving agent.

Figure 1D:
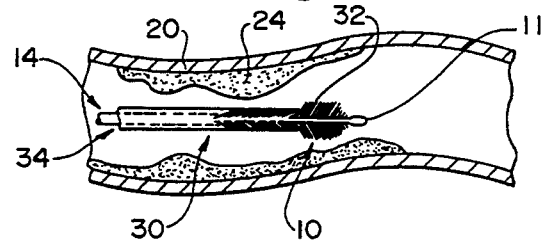

After the treatment is completed, the brush 10 is retracted into the catheter lumen 34 as shown in FIG. 1D, and the drive shaft 14 is fully or partially withdrawn through lumen 34. The catheter 30 may then be withdrawn in the known manner.

FIGS. 1A–1D thus illustrate these common features of the invention which may be practiced in accordance with the various preferred embodiments of FIGS. 2–6 and equivalent structures and methods.

Figure 2:
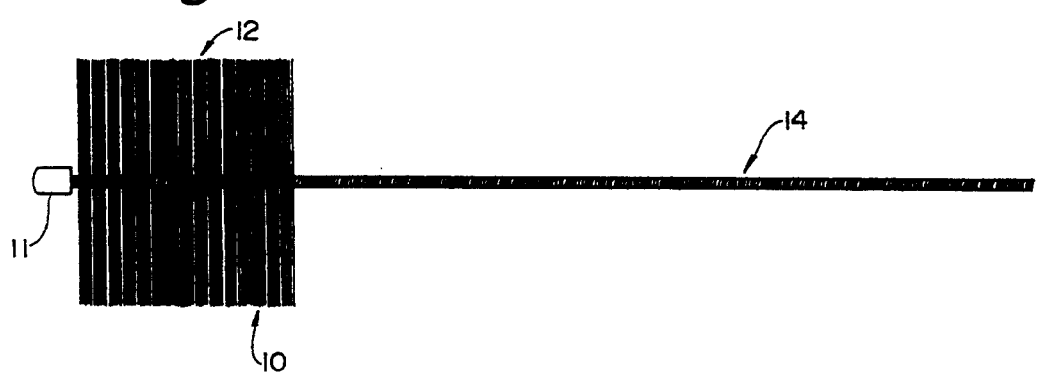
FIG. 2 is a magnified view of one embodiment of a brush and drive shaft suitable for use in the apparatus and method of the invention.
Figure 3:
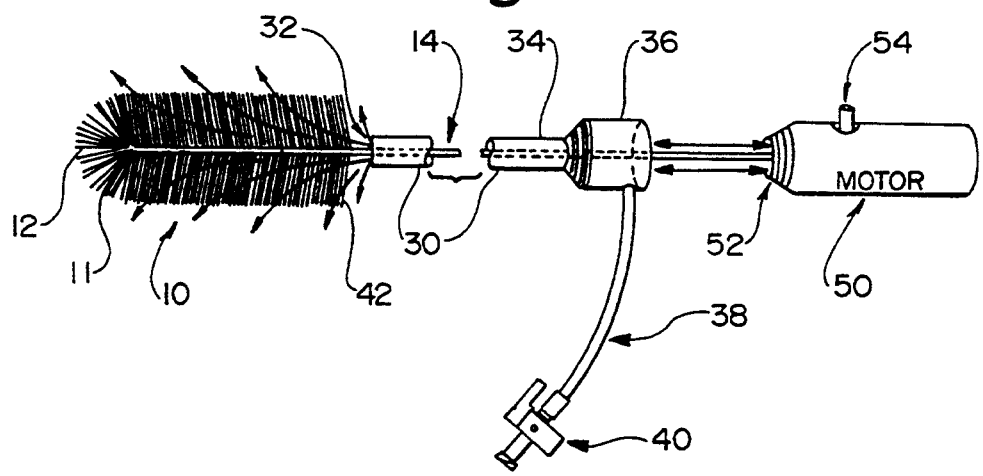
FIG. 3 is a view, in partial cross section, of the assembled components of a first embodiment of the present invention.

Turning to FIGS. 2 and 3, they depict views of somewhat different brushes 10 and distal tips 11 attached to drive shaft 14 useable with a catheter 30 and drive motor assembly 50 in accordance with a first preferred embodiment of the invention. The brush 10 depicted in enlarged detail in FIG. 2 may take the form of a commercially available Millrose nylon bristle brush available from Millrose Corp., Mentor, Ohio. The brush bristles 12 are of a diameter of about 0.003 inches (about 0.075 mm) and are densely packed around the circumference of a short 19 gauge metal shaft 14 to form a brush diameter of about 6.0 mm and length of about 10 mm. The distal tip 11 shown in FIG. 2 extends beyond the brush bristles and may be bulbous to inhibit vessel 20 perforation. In the alternative brush and tip configuration of the embodiment of FIG. 3, the bristles 12 extend all the way to and extend distally from the distal end 11.

In either case, the drive shaft 14 is preferably a solid wire or a cable of stranded wire that has an outside diameter of about 0.50 mm and a length of about 60–120 cm. At the proximal end of the drive shaft 14, a drive motor assembly 50 is intended to be attached by an internal chuck to a proximal portion of the drive shaft 14 so that the entire drive shaft 14 and attached brush 10 may be selectively rotated. The drive motor assembly 50 may be a of the type used for the Simpson Atherocath atherectomy devices by Devices for Vascular Intervention, Inc. or Omnicath by American Biomed, Inc. on and having a unitary housing with a Leur-Lock connector element 52 and on-off button 54 for one hand guiding and operation. The drive motor assembly 50 receives and rotates the drive shaft 14 relatively slowly, on the order of about 10–300 RPM.

The introducer catheter 30 preferably may be a 30 cm long, 6 French O.D. catheter having a Leur-Lock hub 36 with a side port extension 38 attached at its proximal end supplied by Cordis, Corp. The Leur-Lock side port extension 38 terminates in a valved fluid connector 40 having a receptacle formed therein for attachment to a source of dissolving agent.

The Leur-Lock hub 36 and introducer catheter 30 remains stationary while the drive shaft 14 and brush 10 are rotated by the motor 50. The hub 36 is adapted to have a penetrable, self sealing hemostasis valve to receive and seal against the drive shaft 14 and may have a connector to fit on a mating connector element 52 of the drive motor housing to seal the hub 36 and motor from dissolving agent back flow. The dissolving agent passes through the valve 40, into the Leur-Lock hub 36 and down the lumen 34 to be released through the distal opening 32 in a fluid release pattern shown in FIG. 3 by the diverging lines extending through the bristles 12 and designated 42.

In use, the brush and drive shaft of FIGS. 2 and 3 are assembled and advanced through the introducer catheter lumen 34 until positioned as described above and in reference to FIG. 1C. Thus the drive motor 50 and proximal end of the drive shaft 14 may be manipulated back and forth with respect to the introducer catheter 30 as shown by the arrows extending between the Leur-Lock hub 36 and motor 52 in FIG. 3. The introduction and movement of the distal components may be observed under fluoroscopy since the shaft 14 and the distal tip 11 (which may be bulbous) are radio opaque. The drive shaft 14 is attached to the drive motor assembly 50 which is then turned on to effect rotation of the brush bristles 12. The valve of the connector 40 is opened to infuse the dissolving agent through the distal opening 32 in the pattern of lines 42.

In the preferred embodiment of the invention, no further apparatus is employed or steps taken to dissolve the soft obstruction or thrombus in situ. It is expected that the treatment will be commenced within hours of the onset of diagnosis, and the thrombus will be dissolved by the brushing action continually exposing the fibrin of the obstruction to the dissolving agent. To the extent that fragments are created, the agent should dissolve them before they are swept away by blood flow.

Figure 4:
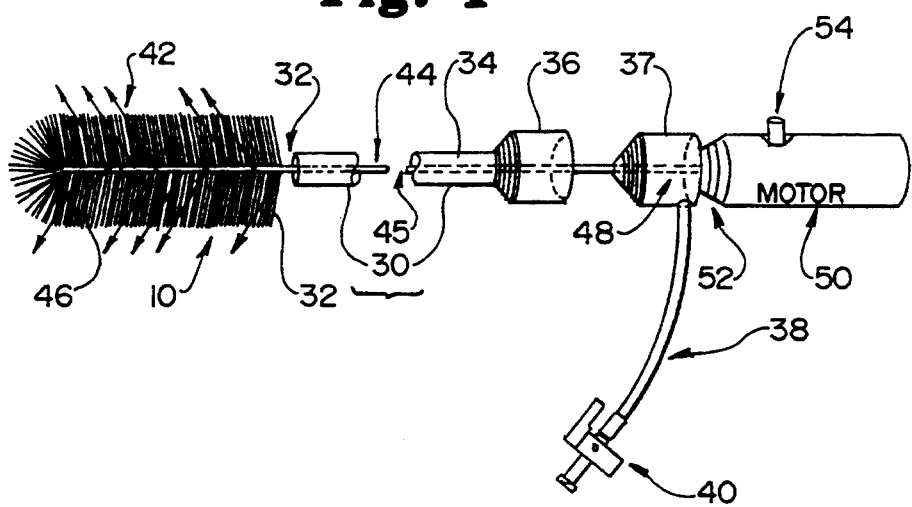
FIG. 4 is a view of the assembled components of a second embodiment of the invention.

In a first alternative embodiment of the dissolving agent infusion apparatus, illustrated as part of the embodiment of FIG. 4, hollow, tubular drive shaft 44 is substituted for the drive shaft 14, and the dissolving agent is introduced into a lumen 45 extending down the length of the hollow drive shaft 60 and exits a series of ports 46 within the bristles 12. The brush 10 and hollow drive shaft 44 are introduced through the Leur-Lock hub 36 and lumen 34 of the introducer 30 to position the brush with respect to the thrombus as described above.

In this case, the dissolving agent must be introduced through the separate Leur-Lock hub 37 which remains in proximity or attached to motor housing 52 while they are moved back and forth together with respect to the introducer catheter 30 and its Leur-Lock hub 36 to withdraw or advance the drive shaft 60 and distal brush 10. The dissolving agent is introduced into the lumen 45 of the hollow drive shaft 44 which is rotated with respect to the hubs 36 and 37 by the motor 50. The hollow drive shaft 44 is attached at its proximal end to the motor 50, and the proximal end portion of the lumen 45 coupled to the drive motor 50 is closed to prevent flow into the motor 50. Ports 48 are provided in the portion of the drive shaft 44 within the Leur-Lock hub 37, so that the dissolving agent introduced through valve 40 and extension 38 into the hub 37 may enter the lumen 45 as the drive shaft 44 rotates with respect to the Leur-Lock hub 37. To prevent leakage of the dissolving agent, the hub 37 may be provided with O-ring seals to allow the rotation of the drive shaft 44 through the hub 37.

In the further embodiments of FIGS. 5, 5A and 6, provision is made for the use of a coaxially introduced guide wire and/or a further small diameter, coaxially introduced, blood flow obstruction catheter to aid in positioning the brush 12 and/or to restrict flow of blood and dissolving agent from the site in order to reduce the amount of agent used and to shorten the time of the procedure, respectively. Consequently, in these embodiments a rotatable drive shaft catheter 60, having at least one drive shaft lumen 62 extending from the hub 37 to the distal end opening 64 thereof, may be substituted for the hollow drive shaft 44 having valves formed internally at the proximal and distal ends thereof for sealing the lumen 62 with or without an inserted guide wire or obstruction catheter.

In this regard, the distal valve also prevents the escape of the dissolving agent out the distal opening 64 of the catheter lumen 62. As shown in the enlarged view of FIGS. 5A and 6, flap valve leaflets 90 are provided through which the shaft 80 of either a guide wire or obstruction catheter may be advanced. A similar set of valve leaflets are formed but not shown at the proximal end of drive shaft catheter 60. The valve leaflets 90 are configured to be normally closed in the absence of a guide wire or catheter and to seal around the outer surface of the guide wire or catheter, if the latter are inserted through the valve leaf to avoid leakage. The construction of such flap valve leaflets of single and multi-lumen catheters for allowing the passage of guide wires and catheters are well known and may take the form of the tri-leaflet valve shown in my U.S. Pat. No. 5,085,635. In use, after the distal end of drive shaft catheter 60 is positioned using a guide wire, the guide wire is withdrawn and the valve leaflets 90 close so that the dissolving agent only exits the sidewall openings 68 into the base of the brush bristles.

In these alternate configurations, the drive shaft catheter 60 is configured at its proximal end in the fashion described above with respect to the Leur-Lock hub 37 and motor 50, except that the obstruction in the proximal end portion of the lumen 62 is replaced by the proximal valve leaflets. The dissolving agent introduced into hub 37 and access ports 61 travels down lumen 62 and is infused out the series of sidewall openings 68 provided in the distal end of the drive catheter 60 in the embodiment of FIGS. 5 and 5A. The sidewall openings 68 are arranged at and proximal and/or distal to the bristles 12 to distribute the dissolving agent more evenly over the bristle surfaces in the fluid release patterns illustrated by arrows 42 as described above with respect to FIG. 4.

As a further variation on the emission of the dissolving agent in the region of the brush 10 illustrated in FIG. 6, hollow fiber brush bristles 12' may be employed which extend into the lumen of the hollow drive catheter 60. Small diameter, flexible hollow fibers of the type employed in blood oxygenators and dialysis equipment may be employed as hollow brush bristles 12'. The dissolving agent may be transported by pressure and osmosis to the tips and out the sides of the hollow brush bristles 12. The hollow fibers may comprise all or part of the bristles 12' of the brush 10 and emit the dissolving agents laterally in the depicted fluid release pattern of the arrows 42'.

In high flow rate blood vessels, it may prove desirable to obstruct the flow of blood and dissolving agent away from the site or trap fragments from being swept away during the introduction of the dissolving agent and while the thrombus is being brushed. In such a situation, the obstruction catheter 80 preferably comprises a balloon catheter having an expandable balloon 82 as also depicted in FIG. 5. In FIG. 5, advantage is taken of the innermost drive shaft catheter lumen 62 to introduce the deflated balloon 82 on a catheter shaft 80 having a distal end 84 and a proximal end 86 and hub 88 for inflating the balloon after it is positioned. Inflation to a low pressure sufficient to block the majority of downstream blood flow temporarily enables the dissolving agent to be kept in place and complete dissolution of the thrombus more rapidly and minimize the amount of dissolving agent used.

In use, the balloon catheter with an expandable balloon 82 may be inserted, with the balloon 82 deflated, through the drive catheter lumen 62 after it is positioned and extended past the thrombus 22 as shown in FIGS. 1A–1D. Inflation of the balloon 82 downstream of the thrombus 22 would block blood flow and escape of the dissolving agent and fibrin fragments during the infusion and brushing steps.

Although not specifically illustrated, the obstruction mechanism may take other forms. In a first variation, an expandable wire basket can be mounted on a fine 0.035 inch (0.85 mm) guide wire and positioned downstream of the thrombus 22 in the blood vessel 20 depicted in FIGS. 1A–1D. After the brush 10 is positioned as described above, the guide wire mounted basket and mesh assembly could be introduced through drive catheter lumen 62 in a compressed state and advanced distally of the soft thrombus 22 and expanded. Thereafter, as the obstruction 22 is brushed and infused with dissolving agent, blood, the agent itself, and fibrin fragments breaking free of the thrombus 22 would be restricted from flowing away. The dissolving agent would continue to act on them.

During the rotation of the drive shaft catheter 60, the proximal end hub 88 may be locked in place so that the catheter 80 does not tend to rotate with it. Slippage between the rotating catheter 60 and the stationary catheter 80 is allowed by the valve leaflets 90 at the distal end and the similar valve leaflets at the proximal end bearing against the outer surface of the catheter 80.

In all of the preferred embodiments and variations thereof, the battery operated drive motor allows rotation at about 10-300 revolutions per minute. The brush bristles are soft and flexible and preferably vary in length to present a brush of about 2-10 mm in diameter.

The brush bristles separate the soft thrombus and may bear against the intima of the blood vessel. The bristles are incapable of penetrating the blood vessel, but may cause minor abrasion and irritation. This ordinarily will not lead to complications.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

PARTS LIST brush 10
distal shaft tip 11
bristles 12
hollow fiber bristles 12'
drive shaft 14
blood vessel 20
thrombus 22
plaque 24
introducer catheter 30
distal opening 32
introducer lumen 34
Leur-Lock hub 36
Leur-Lock hub 37
side port extension 38
valve 40
fluid release pattern arrows 42
fluid release pattern arrows 42'
hollow drive shaft 44
drive shaft lumen 45
fluid exit ports 46
access ports 48
drive motor assembly 50
connector element 52
on-off button 54
rotatable drive catheter 60
access ports 61
drive catheter lumen 62
distal end opening 64
sidewall openings 68
blocking catheter 80
blocking balloon or mesh assembly 82
distal end 84
inflation openings 85
proximal end 86
proximal hub 88
valve 90

What is claimed is:

1. A thrombectomy system for dissolving a soft, fibrinous obstruction, such as a recently formed thrombus or blood clot, within a patient's vascular system comprising:
   a brush having bristles sufficiently dimensioned and stiff to separate the fibrin of the soft obstruction as the bristles are passed therethrough;
   means for introducing the brush into contact with the soft obstruction and for repetitively passing the bristles of the brush through the soft obstruction so as to expose the fibrin of the obstruction; and
   means for introducing a dissolving agent into contact with the soft obstruction as the fibrin thereof are exposed by the bristles of the brush.

2. The system of claim 1 wherein said brush further comprises:
   an elongated drive shaft having a proximal and a distal end and having said bristles mounted to extend radially from a portion of said distal end.

3. The system of claim 2 wherein said elongated drive shaft further comprises an elongated drive shaft lumen extending from said proximal to said distal end thereof, said shaft lumen having at least one aperture at said distal end.

4. The system of claim 3 wherein said dissolving agent introducing means further comprises:
   means for communicating with said shaft lumen for passing said dissolving agent therethrough and out said at least one aperture.

5. The system of claim 4 wherein said at least one aperture is formed in the side of said drive shaft in the distal end adjacent to said radially extending bristles for introducing said dissolving agent in close proximity to said brush bristles passing through said soft obstruction.

6. The system of claim 4 wherein said brush bristles are formed of hollow fiber bristles extending from said drive shaft lumen for introducing said dissolving agent through said hollow fiber bristles in close proximity to said brush bristles passing through said soft obstruction.

7. The system of claim 1 wherein said introducing means further comprises an elongated introducer catheter having a proximal and a distal end and an introducer lumen extending therebetween, said introducer catheter adapted to be introduced and advanced through a patient's blood vessels until the distal end is positioned adjacent a soft fibrinous obstruction, and said introducer lumen adapted to receive said brush advanced therethrough.

8. The system of claim 7 wherein said dissolving agent introducing means further comprises:
   coupling means attached at the proximal end of said introducer catheter for introducing said dissolving agent into said introducer lumen for emission from the distal end thereof during rotation of said brush.

9. The system of claim 1 further comprising:
   means for temporarily restricting the flow of blood and dissolving agent and un-dissolved fibrin fragments broken free by action of the brush bristles from the region of the obstruction to allow the dissolving agent to complete the dissolution of the fibrinous obstruction.

10. The system of claim 9 wherein said restricting means further comprises:
    an inflatable balloon for blocking, when inflated, the flow of un-dissolved fibrin fragments broken free by action of the brush bristles from the region of the obstruction to allow the dissolving agent to complete the dissolution thereof;
    means for introducing said inflatable balloon in a deflated state past the soft obstruction; and
    means for inflating said balloon in order to block the patient's blood vessel.

11. A thrombectomy system for dissolving a soft fibrinous obstruction, such as a recently formed thrombus or blood clot, from a patient's vascular system comprising:

an elongated introducer catheter having a proximal and a distal end and an introducer lumen extending therebetween, said introducer catheter adapted to be introduced and advanced through a patient's blood vessels until the distal end opening is positioned adjacent a soft fibrinous obstruction;

an elongated, flexible, rotatable drive shaft having a proximal and a distal end portion and adapted to be passed through said introducer lumen;

a brush formed at the distal end portion of said drive shaft having soft, flexible bristles extending outward from said distal end portion a predetermined distance, said bristles being sufficiently resilient and dimensioned for enabling compression and passage of the brush through said introducer lumen and out of and back into said distal end opening of said introducer lumen;

means for rotating said drive shaft at said proximal end thereof, whereby said brush may be rotated when advanced out of said distal end opening of said introducer lumen and into contact with a soft obstruction within the patient's blood vessel; and means for introducing a dissolving agent in the region of rotation of said brush for dissolving the soft obstruction as it is contacted by said bristles.

12. The system of claim 11 further comprising:
means for temporarily restricting the flow of blood and dissolving agent and un-dissolved fibrin fragments broken free by action of the brush bristles from the region of the obstruction to allow the dissolving agent to complete the dissolution of the fibrinous obstruction.

13. The system of claim 12 wherein said restricting means further comprises:
means for introducing said restricting means through said soft obstruction and distal to said brush.

14. The system of claim 11 wherein said dissolving agent introducing means further comprises a Luer-lock hub and a side port extension and valve coupled to said introducer lumen and distal aperture for introducing said dissolving agent therethrough and in close proximity to said brush bristles contacting said soft obstruction.

15. The system of claim 11 wherein said brush bristles are mounted to extend radially from said distal end of said drive shaft.

16. The system of claim 11 wherein said elongated drive shaft further comprises an elongated shaft lumen extending from said proximal to said distal end thereof, said shaft lumen having at least one aperture at said distal end.

17. The system of claim 16 wherein said dissolving agent introducing means further comprises:
means for communicating with said drive shaft lumen for passing said dissolving agent therethrough.

18. The system of claim 17 wherein said at least one aperture is formed in the side of said drive shaft in said distal end adjacent to said radially extending bristles for introducing said dissolving agent in close proximity to said brush bristles contacting said soft obstruction.

19. The system of claim 11 wherein:
said elongated drive shaft further comprises an elongated shaft lumen extending from said proximal to said distal end thereof;
said dissolving agent introducing means further comprises access ports for communicating with said drive shaft lumen for passing said dissolving agent therethrough; and said brush bristles are formed of hollow fiber bristles extending from said drive shaft lumen for introducing said dissolving agent through said hollow fiber bristles in close proximity to said brush bristles passing through said soft obstruction.

20. The system of claim 11 wherein:
said elongated drive shaft further comprises:
an elongated shaft lumen extending from said proximal to said distal end thereof, said shaft lumen having proximal and distal end openings and at least one aperture in the distal end portion of said drive shaft; and
proximal and distal, penetrable valve means formed in said shaft lumen adjacent to said proximal and distal end openings, said valve means obstructing the flow of dissolving agent from said end openings;

and wherein said introducing means further comprises:
hub means coupled to said drive shaft in the proximal portion thereof for introducing said dissolving agent into said drive shaft lumen, whereby said dissolving agent is emitted from said at least one aperture in said distal end portion adjacent to the brush bristles.

21. The system of claim 20 further comprising:
restricting means penetrable through said proximal and distal valve means and extendable through said elongated drive shaft lumen and distally from said distal end opening for temporarily restricting the flow of blood and dissolving agent and un-dissolved fibrin fragments broken free by action of the brush bristles from the region of the obstruction to allow the dissolving agent to complete the dissolution of the fibrinous obstruction.

22. The system of claim 21 wherein said restricting means further comprises:
an inflatable balloon for blocking, when inflated, the flow of dissolving agent, blood and un-dissolved fibrin fragments broken free by action of the brush bristles from the region of the obstruction to allow the dissolving agent to complete the dissolution thereof;
means for introducing said inflatable balloon in a deflated state through said drive shaft lumen and past the soft obstruction; and
means for inflating said balloon in order to block the patient's blood vessel.

23. The system of claim 20 wherein said at least one aperture comprises a plurality of apertures and wherein:
said brush bristles are mounted to extend radially from said distal end of said drive shaft including a plurality of hollow fiber bristles extending from said plurality of apertures for emitting said dissolving agent from said hollow fiber bristles.

24. A thrombectomy method for dissolving a soft, recently formed fibrinous obstruction, such as a thrombus or blood clot, within a patient's vascular system comprising the steps of:
introducing a mixing brush though the patient's vascular system into contact with the soft fibrinous obstruction;
passing bristles of the mixing brush through the soft fibrinous obstruction to effect the separation and exposure of the fibrin thereof; and introducing a dissolving agent into the soft fibrinous obstruction as the bristles of the mixing brush are passed therethrough for dissolving the fibrin of the obstruction as the fibrin is separated and exposed to the dissolving agent.

25. The method of claim 24 wherein:

the step of introducing the mixing brush further comprises:

introducing an elongated introducer catheter, having an introducer lumen extending between the proximal and a distal end, through the vascular system of the patient to position the distal end thereof adjacent to the soft obstruction; and passing the brush through said lumen and from the distal end of the introducer catheter so that the bristles thereof are in contact with the soft obstruction; and the step of passing the bristles through the soft fibrinous obstruction further comprises:

rotating the brush so that the bristles rotate and brush through the soft fibrinous obstruction.

26. The method of claim 25 wherein the step of introducing a dissolving agent further comprises:

introducing the dissolving agent through openings in the brush.

27. The method of claim 24 wherein the step of introducing a dissolving agent further comprises:

introducing the dissolving agent through openings in the bristles of the brush.

28. The method of claim 24 further comprising the step of:

blocking the flow of dissolving agent, blood and undissolved fibrin fragments broken free by action of the brush bristles from the region of the soft obstruction during introduction of the dissolving agent to allow the dissolving agent to complete the dissolution thereof.

29. The method of claim 28 wherein said blocking step further comprises:

introducing an inflatable balloon in a deflated state past the soft obstruction;

inflating said balloon to block the patient's blood vessel during the steps of brushing and dissolving the soft obstruction; and deflating and withdrawing said balloon upon completion of the steps of brushing and dissolving the soft obstruction.

30. The method of claim 24 wherein the introducing and passing steps further comprise:

introducing the elongated introducer catheter through the soft obstruction;

passing the brush out the distal end opening of the introducer lumen;

retracting the introducer catheter back through the obstruction; and retracting the brush so that the brush bristles bear against the obstruction while the brush is rotated and the dissolving agent is introduced.

31. A thrombectomy method for dissolving a soft, recently formed, fibrinous obstruction, such as a thrombus or blood clot, within a patient's vascular system comprising the steps of:

introducing and advancing an elongated, introducer catheter having a proximal and a distal end and an introducer lumen extending therebetween through a patient's vascular system until the distal end is positioned adjacent a soft fibrinous obstruction;

passing an elongated, flexible, rotatable drive shaft, having a proximal end portion and a distal end portion having a brush attached thereto, the brush having soft, flexible bristles extending outward from said distal end portion a predetermined distance, said bristles being sufficiently resilient and dimensioned for enabling compression and passage of the brush through said introducer lumen until said brush bristles are extended out of said distal end of said introducer lumen and into contact with a soft fibrinous obstruction;

rotating said drive shaft at said proximal end thereof, whereby the bristles of said brush are rotated through the fibrin of said obstruction to separate the fibrin; and introducing a dissolving agent in the region of rotation of said brush for dissolving the fibrin of the soft obstruction as they are separated by said rotating bristles.

32. The method of claim 31 wherein the introducing and passing steps further comprise:

introducing the elongated introducer catheter through the soft obstruction;

passing the brush out the distal end of the introducer lumen;

retracting the introducer catheter back through the obstruction; and retracting the brush so that the brush bristles bear against the obstruction while the brush is rotated and the dissolving agent is introduced.

33. The method of claim 31 wherein the step of introducing a dissolving agent further comprises:

introducing the dissolving agent through openings in the brush.

34. The method of claim 31 wherein the step of introducing a dissolving agent further comprises:

introducing the dissolving agent through openings in the bristles of the brush.

35. The method of claim 31 wherein the step of introducing a dissolving agent further comprises:

introducing the dissolving agent through the introducer lumen of said introducer catheter.

36. The method of claim 31 further comprising the step of:

blocking the flow of dissolving agent, blood and undissolved fibrin fragments broken free by action of the brush bristles from the region of the soft obstruction during introduction of the dissolving agent to allow the dissolving agent to complete the dissolution thereof.

37. The method of claim 36 wherein said blocking step further comprises:

introducing an inflatable balloon in a deflated state past the soft obstruction;

inflating said balloon to block the patient's blood vessel during the steps of brushing and dissolving the soft obstruction; and deflating and withdrawing said balloon upon completion of the steps of brushing and dissolving the soft obstruction.

* * * * *